United States Patent [19]

Carter et al.

[11] Patent Number: 4,797,368

[45] Date of Patent: Jan. 10, 1989

[54] ADENO-ASSOCIATED VIRUS AS EUKARYOTIC EXPRESSION VECTOR

[75] Inventors: Barrie J. Carter, Kensington, Md.; Jon D. Tratschin, Berne, Switzerland

[73] Assignee: The United States of America as represented by the Department of Health and Human Services, Washington, D.C.

[21] Appl. No.: 712,236

[22] Filed: Mar. 15, 1985

[51] Int. Cl.⁴ .................. C12N 7/00; C12N 15/00; C12P 19/34; C12P 21/00

[52] U.S. Cl. .................. 435/320; 435/68; 435/70; 435/91; 435/172.3; 435/317; 435/235; 935/32; 935/34; 935/57; 536/27

[58] Field of Search ............ 435/172.3, 240, 317, 435/68, 235, 91, 70, 320, 235; 935/22, 33, 56, 57, 32, 34

[56] References Cited

U.S. PATENT DOCUMENTS 4,419,446 12/1983 Howley et al. .................. 435/172.3

OTHER PUBLICATIONS

Tratschin, J. et al. (Sep. 1984) J. Virol 51:611-619.
Tratschin, J. et al. (Oct. 1984) Molec. Cell. Biol. 4:2072-2081.
Hermonat, P. and N. Muzyczka (Oct. 1984) PNAS 81:6466-6470.
Laughlin et al., Gene, 23 (1983) 65-73.

Primary Examiner—Thomas G. Wiseman
Assistant Examiner—Stephanie Seidman
Attorney, Agent, or Firm—Holman & Stern

[57] ABSTRACT

The present invention relates to a vector comprising part of AAV DNA contained in a plasmid and capable of being packaged into AAV particles and functioning as a vector for stable integration and expression of a gene in eukaryotic cells when under control of an AAV transcription promoter. A method of preparing such plasmids which are packagable and rescuable is also described.

4 Claims, 1 Drawing Sheet

ADENO-ASSOCIATED VIRUS AS EUKARYOTIC EXPRESSION VECTOR

BACKGROUND OF THE INVENTION

1. Technical Field

The present invention is related to a eukaryotic vector for stable maintenance or expression of DNA sequences or genes in eukaryotic cells. More particularly, the present invention is related to a vector based on the parvovirus, adeno-associated virus (AAV), wherein said vector is packaged into AAV particles. Such particles, when used to infect eukaryotic cells, allow maintenance or expression of DNA sequences or genes at a high frequency. The vector of the present invention is also rescuable from eukaryotic cells

2. Prior Art:

Heretofore, the use of a parvovirus as an expression vector was not known. Other virus-based eukaryotic expression vectors have been described (*Eukaryotic Viral Vectors*, ed Y. Gluzman, (Cold Spring Harbor Laboratory, N.Y. 1982). However, the other vectors described so far have one or more disadvantages: (a) They do not integrate a foreign gene into the host cell genome at high frequency; (b) are not easily rescuable from the integrated state, or (c) are limited in their host range either for expression or for rescue, or (d) include many other viral genes as well which may complicate analysis of the particular gene under study.

Some studies have shown that a gene inserted into a viral-based vector can be introduced into mammalian cells at high frequency using DNA transfection procedures rather than packaging into a virus particle. However, these transfection procedures result in integration of the gene together with flanking sequences derived from plasmid DNA and generally suffer from the problem of inability to be easily rescued. An additional difficulty with this procedure is that some cells transfect very poorly and indeed some transfection procedures are toxic to certain cell types. In contrast, AAV particles have a high probability of infecting most cell types very efficiently.

Samulski et al., (Proc. Natl. Acad. Sci. USA 1982, 79: 2077) reported construction of a plasmid vector using GC tailing. As would be evident from the detailed description infra of the present invention, the Samulski et al procedure is quite different. Samulski et al., employ GC tailing while the present invention utilizes molecular linkers.

An advantage of the present invention is that AAV can be excised intact, free of plasmid sequence by cleavage in vitro. This is not possible by prior art methods including the Samulski, et al procedure.

Laughlin et al., (Gene, 1983, 23: 65–73) described the construction and cloning of infectious adeno-associated virus (AAV) genomes in bacterial plasmids and speculated on the potential of AAV as a eukaryotic vector. However, an actual rescuable system demonstrating the functional feasibility of an AAV as a eukaryotic vector for introduction and stable expression of genes in eukaryotic cells has not heretofore been known or disclosed.

The present invention for the first time establishes AAV as a system useful as a vector either for transient expression or for site-specific mutagenesis as well as for stable maintenance or expression of foreign DNA sequences or genes in eukaryotic cells. By "foreign DNA sequences or genes", it is meant any DNA sequence other than those in normal wild type AAV.

SUMMARY OF THE INVENTION

It is, therefore, an object of the present invention to provide a vector for the expression of genes when integrated into eukaryotic cells.

It is another object of the present invention to provide an adeno-associated virus as an eukaryotic expression vector.

It is a still further object of the present invention to provide a eukaryotic expression vector capable of expressing an integrated gene at high frequency.

It is yet another object of the present invention to provide a eukaryotic vector rescuable from cells carrying the integrated vector.

It is a further object of the present invention to provide a method for preparing a packagable and rescuable eukaryotic vector capable of expressing an integrated gene at high frequency.

It is a still further object of the present invention to express a gene from an AAV transcription promoter.

It is an additional object of the present invention to provide a method of introducing or integrating genes into host cells solely on the basis of phenotypic expression without the necessity of nucleic acid probe, sequence information or testing of the product controlled by the integrated gene.

Other objects and advantages will become apparent as the detailed description of the invention proceeds.

BRIEF DESCRIPTION OF THE DRAWINGS

These and other objects, features and many of the attendant advantages of the invention will be better understood upon a reading of the following detailed description when considered in connection with the accompanying drawing wherein.

DETAILED DESCRIPTION OF THE INVENTION

Figure 1:
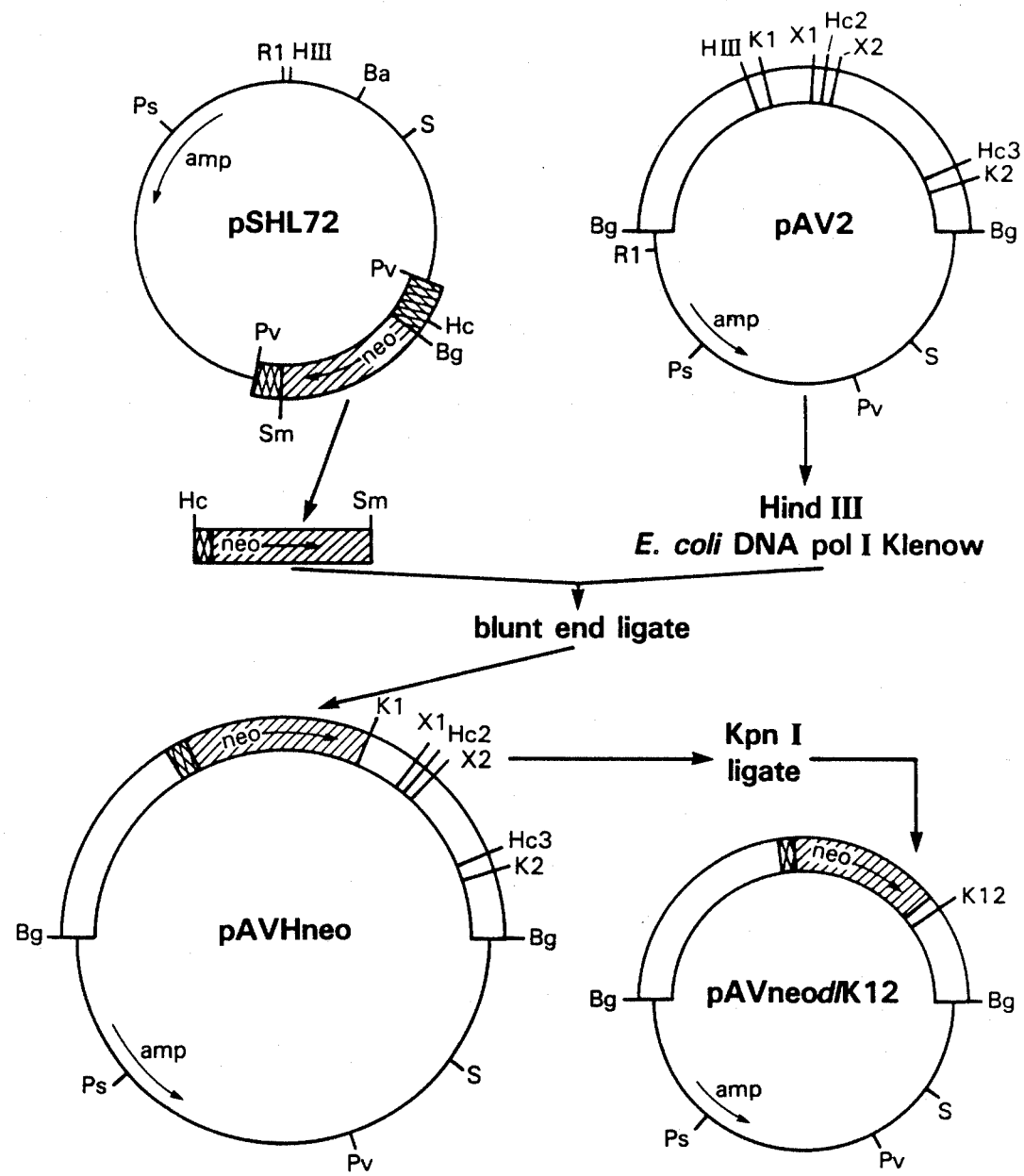
FIG. 1 shows a schematic construction of a eukaryotic vector in accordance with the present invention. The circles indicate recombinant plasmids. The derivation of DNA sequences is designated as follows: single line-pBR322 DNA; double line-AAV2 DNA; diagonally shaded line-neo gene from bacterial transposon Tn5; cross-hatched-HSV1 thymidine kinase gene. The arrow indicates the direction of transcription of the neo gene. Relevant restriction endonuclease sites are shown and designated: Ps, PstI; Rl, EcoRI; HIII, HindIII; Ba, BamHI; S, SaI; Pv, PvuII; Hc, HincII; Bg. BglII; Sm, SmaI; X, XhoI; K,KpnI. For AAV, the X, K and Hc sites are distinguished by an additional numeral e.g. X1, X2.

These and other objects and advantages of the present invention are achieved by a eukaryotic expression vector for introduction and stable expression of genes in eukaryotic cells and a method of preparing such expression vectors.

Vectors suitable for the expression of genes in eukaryotic cells can be based on RNA viruses (retroviruses) or DNA viruses. Examples of such DNA viruses include papovavirus, adenovirus, herpesvirus, poxvirus and the like. Among the DNA viruses the defective, human parvovirus designated adeno-associated virus (AAV) is a novel eukaryotic vector (parvector) for the expression of foreign genes in human, mammalian and other eukaryotic cells.

As noted above, AAV is a defective human parvovirus and grows only in cells which are also infected with a helper virus (adenovirus or herpesvirus). Replication of AAV is limited only by the host range of the helper. AAV grows in a wide variety of human, simian and rodent cells if the appropriate helper virus is used. In the absence of helper virus, infection of cells with AAV results in integration of the AAV genome into the cell chromosome. Cells carrying an integrated AAV genome show no change in cell growth or morphology. If helper virus is added to cells carrying an integrated AAV genome, the AAV can be rescued and replicated to produce infectious virus particles. These observations led to the development and demonstration as described herein that AAV can be used as a high-frequency eukaryotic vector.

A summary of major steps in the preparation of a eukaryotic vector using AAV for integration and rescue of foreign genes in accordance with the present invention is now described. All publications cited hereunder are incorporated herein by reference. The vector comprises a foreign gene inserted under control of an AAV promoter in an AAV derived genome contained in a plasmid molecule.

1. Construction of AAV vectors containinq foreign DNA:

(a) The starting point is obtaining a recombinant DNA molecule containing an AAV genome joined to a plasmid, such construct capable of being grown in a host bacterium. An example of such a plasmid is pAV2 and of a host bacterium is *E. coli*. Insertion of the foreign DNA sequence is accomplished by standard techniques (Maniatis et al in Molecular Cloning, 1982, Cold Spring Harbor Laboratory, N.Y.) into a site in the AAV sequence such that the inserted sequence is expressed under the control of a transcription promoter. It is noted here that this vector may also be used for introduction of DNA sequences which are not expressed transcriptionally, in which case it is not necessary to have them under control of a transcription promoter.

(b) If the construct is too large, then a portion or portions of the AAV sequence are deleted from the construct to allow the combined AAV-foreign DNA sequence, but excluding the plasmid sequence, to be small enough to be packaged into an AAV particle. Of course, one can also begin with a deletion mutant and then proceed with step (a) above.

(c) Various regions of the AAV genome may be deleted in these vectors both in the right half of the genome, (map units 40-92) as for instance in the construct pJDT55 (pAVdlk12) vide infra, or in the left half of the genome (map units 40-92) or in both halves.

(d) Vectors with deletions in the right half of AAV genome sequence cannot make AAV capsid protein, hence for packaging or rescue must be complemented with a plasmid or AAV genome that can provide this function.

(e) Vectors with deletions in the left half of the AAV genome sequence cannot replicate AAV DNA and for packaging or rescue must be complemented with a plasmid or AAV genome that can provide this function.

A preferred AAV vector suitable as a starting material fo the practice of the present invention is pAVdlk12 which is in deposit at the American Type Culture Collection, Rockville, MD under accession number 39999. This deposited AAV vector can be employed for the insertion of any gene in a manner analogous to that of the neo gene construction exemplified herein.

(f) This vector can be directly introduced into eukaryotic cells by any standard method, e.g., transfection, microinjection, protoplast fusion and the like.

(g) An alternate procedure for obtaining expression of integrated gene at high frequency in accordance with the present invention is described hereunder.

2. Packaging of AAV vectors into AAV particles and introduction in cells:

(a) The vector DNA is transfected (McCutchan and Pagano, 1968, J. National Cancer Institute, 41,351-7; Wilger et al, 1979, PNAS, 76:1373-1376) into permissive eukaryotic cells (usually human cells) in the presence of a complementing AAV genome or recombinant AAV-plasmid which can supply either of the necessary functions described in steps 1(d) or 1(e) above and also in the presence of a helper virus, usually an adenovirus.

(b) After several days the cells are harvested, frozen and thawed repeatedly and heated at 60° C. for 15 minutes to inactivate the adenovirus helper. This cell lysate contains AAV particles having the AAV vector packaged in AAV particles. Particles containing the AAV vector can be further purified, or the lysate may be used directly or the number of particles may be amplified by additional passages of this virus stock in permissive cells.

(c) To introduce the vector into eukaryotic cells, the particle lysates from step 2b are used to infect cells using standard virus infection protocols.

(d) Selection of cells expressing the gene contained in the vector may be performed in several ways. If the foreign gene is a dominant selective marker, the cells may be placed under appropriate selective pressure after infection. Cells which survive the selection contain the gene in a suitable integrated state and express it. If selection is not possible directly then the cells may be subcloned and individual clones may be tested for expression of the desired genes by any other convenient procedure. In many instances, an easily selectable marker gene could be included in the AAV vector as well as the desired second gene. The vector would then be used by first selecting for the marker and then testing these clones for expression or function of the second gene.

3. Rescue of the AAV vector from cells:

(a) The cell cultures or cell lines produced as described in Section 2 containing the AAV vector stably integrated into the cell chromosome, together with its inserted gene, can be rescued.

(b) The vector can be rescued by supplying the cells with helper functions by infecting wih a helper virus (usually adenovirus). For some cell clones or cultures this is sufficient to rescue the vector. In other cases it is necessary also to supply an AAV replication function by infecting the cells with AAV particles or by transfecting with an AAV-plasmid. The rescued DNA can be obtained free of cell DNA, e.g., by extraction with the high salt-detergent lysis (Hirt 1967, J. Mol. Bio. 26: 365–369) procedure or the like well known in the art. If the rescue is performed in the presence of virus particles, the rescued vector can again be packaged into AAV particles.

A critical feature in developing AAV as a high frequency vector for integration and expression of genes in accordance with the present invention is the ability to package the vectors into AAV particles. This requires experimental analysis of sequences which could be deleted from AAV and still allow replication and complementation by either wild type or mutant AAV as well as experimental determination of sites at which coding sequences could be inserted into AAV such that subsequent expression would be under control of the AAV promoter. The packaging can be obtained by transfection of human 293 cells with the AAV vector plasmid construct together with wild type AAV (pAV2) or a non-replicating AAV such as pAVBcBs (Tratschin et al, 1984, J. Virol. 51: 611-619) or a plasmid pAVdlBam, infra. The latter two plasmids help to reduce the amount of wild type AAV particles present in vector-containing particle preparations although there are still wild type AAV genomes generated by recombination.

The vector constructions described here use the wild type conformation of the $p_{40}$ or $p_{19}$ promoters of AAV. However, several possible ways can be employed to elevate the level of expression which may be expected in turn to increase the frequency of phenotypically transformed cells which can be selected.

First, it was found that deletion of sequences upstream of the AAV $p_{40}$ promoter, which inactivate the AAV rep gene product, increases expression from $p_{40}$ by up to 10 fold. Secondly, it was found that the adenovirus VA$_I$RNA gene product increases expression from AAV $p_{40}$ by 20 to 30 fold. Third, it was found that heat-shock of cells also increases expression from $p_{40}$ by several fold. These discoveries suggested several ways to increase the efficiency of the AAV vector system. For instance, a copy of the adenovirus type 2 or type 5 VA$_I$RNA gene (about 160 base pairs) can be inserted into the AAV vector to increase translational expression from $p_{40}$ RNA transcripts. It may also be advantageous to incorporate other transcription promoters into AAV for this purpose.

A construction and an operational cycle using this AAV vector is now described.

Construction of the vector (1) First, the vectors pAVHneo and pAVHneodlk12 were constructed as shown in FIG. 1. These vectors contain the neomycin phosphotransferase II gene (neo) from the prokaryotic transposon Tn5.

(2) The neo gene was obtained by cleaving the plasmid pSHL72 with HincII and SmaI. This generated a 970 base pair fragment (FIG. 1) containing the neomycin phosphotransferase coding region and a few nucleotides of the herpes simplex type I (HSV) thymidine kinase gene at 5 end. However, this fragment does not include the HSV thymidine kinase promoter sequence.

(3) The plasmid pAV2 was cleaved with HindIII at the single HindIII site in the AAV sequence. This cleaved DNA was treated with E. coli DNA polymerase I Klenow fragment to convert the HindIII gnerated cohesive ends to blunt ends. This DNA was then joined to the HincII/SmaI neo fragment under the conditions for blunt-end ligation with T4 DNA-ligase. This ligated DNA preparation was then transfected with E. coli HB101 and grown in ampicillin containing medium to select the plasmid pAVHneo.

(4) From pAVHneo, the AAV2 kpnI fragment between the sites K1 and K2 was removed by cleaving with KpnI followed by ligation with Ty DNA-ligase to generate pAVHneodlk12. This second plasmid was also prepared in bulk by transfection into E. coli HB101.

Description of an operational cycle

To use the vectors pAVHneo and pAVHneodlk12 for introduction of the neo marker into mammalian cells, the cells in culture were directly transfected with the purified vector DNA using the CaPO$_4$ transfection procedure as outlined in Table 1.

The vector pAVHneodlk12 was also packaged into AAV particles by complementing it in a DNA transfection assay with an AAV plasmid that could generate AAV capsid protein. This was performed in the following way:

(1) $5 \times 10^6$ human 293 cells (human embryonic kidney cells transformed with a fragment of adenovirus 5 DNA) growing in a 10 cm plastic petri dish were infected with helper adenovirus 2 (10-20 pfu/cell) and 1 hour later were transfected with pAVHneodlk12 DNA (5 µg) and pAV2 DNA (5 µg) using the CaPO$_4$ transfection procedure. 48 hours after transfection, the cells were harvested from the plate and frozen and thawed three times in a volume of 5 ml to release the viral particles. The lysate was then heated at 60° C. to inactivate adenovirus. This lysate was then used to infect a spinner culture of KB cells (100 ml, $3 \times 10^7$ cells) together with helper adenovirus type 2 (10 pfu/cell) and the culture was grown for 44 hours.

TABLE I

Transformation of Hela Cells to gen$^r$ with an AAV vector.

| Vector | Amount | frequency of gen$^r$ transformants |
| --- | --- | --- |
| pAVHneodlk12 DNA | 7.5 µg/$10^{-6}$ cells | $2.0 \times 10^{-4}$ |
| pAVHneodlk12 DNA | 1000 particles/cell | $4.7 \times 10^{-3}$ |
| pAVHneodlk12 DNA | 100 particles/cell | $4.5 \times 10^{-3}$ |
| pAVHneodlk12 DNA | 10 particles/cell | $1.0 \times 10^{-3}$ |
| pAVHneodlk12 DNA | 1 particles/cell | $1.1 \times 10^{-4}$ | a For each experiment $10^6$ Hela cells were transfected with DNA or infected with particles as indicated. Two days after transfection or one day after infection the cells were split 1:25 and replated with 75 cm plastic T-flasks and grown in Eagle's minimal essential medium containing 10% fetal calf serum and the selective drug geneticin (1 mg/ml, 40% activity). The plasmid DNA preparation and particles containing AVHneodlK12 vector genomes were made by two cycles of growth in KB cells and CsCl purification as described in the text.
b The number of gen$^r$ colonies was counted at 10 to 15 days after placing the cells under selection in geneticin containing medium.
c Note that transfection of $10^6$ cells with 7.5 µg of plasmid DNA is equivalent to 4. $\times 10^7$ genomes per cell.

The cells were then harvested by centrifuging and resuspending in growth medium (10 ml) and again heated to inactivate adenovirus. One half of this lysate was used to infect a spinner culture of KB cells (1 liter, $3 \times 10^8$ cells) together with fresh helper adenovirus. After 44 hours the virus was again harvested and the virus particles were purified by one cycle of banding in CsCl equilibrium density gradient. From the CsCl gradient the region between a density of 1.39 g/cm$^3$ and 1.36 g/cm$^3$ was taken containing packaged AVH-neodlK12 genomes. This fractionation also removed adenovirus and much of the wild type AAV particles. The preparation of particles was dialysed at 4° C. against Tris-HCl, pH 8.0, 0.3M NaCl and then heated at 60° C. to inactivate any residual adenovirus. The approximate number of AAV particles was estimated spectrophotometrically.

(2) The preparation of particles from the above step was used to infect Hela cells (in the absence of any helper adenovirus) as described in Table I. One day after infection the cells were trypsinized and replated in selective growth medium containing the antibiotic geneticin (1 mg/ml, 40% active) to allow growth of those cells only which expressed the neo gene. Geneticin-resistant colonies (gen$^r$) were counted at 10-14 days. The results of a particular experiment are shown in Table I. In Hela cells, neo cells were obtained at a frequency of about 25 fold more than when the same cell lines were transfected with the parental plasmid DNA pAVHneodlK12.

(3) The AAV-neo vector was stably integrated in the host cell genome as determined by the absence of detectable free copies in Hirt extracts made of gen$^r$ cells and preliminary analysis by the Southern blotting technique of restriction endonuclease cleavage patterns of bulk DNA extracted from such cells.

The integrated AAV-neo vector (AVHneodlK12) is rescuable because infection of the gen$^r$ cells with helper adenovirus together with infection by wild type AAV particles resulted in excision and replication of AAV-neo genomes that could be isolated in a Hirt extract. It may also be noted that from gen$^r$ colonies generated by AAV neo vector, the vector was also rescuable from the qenr cells by packaging into AAV particles.

In the examples described above the AVHneodlK12 vector was packaged into AAV particles by complementation with pAV2 DNA. Similarly the AVHneodlK12 vector was also packaged into AAV particles by complementation with other AAV plasmids such as the plasmid pPS12 which cannot replicate due to a cis-dominant replication defect or the plasmid pAVdlBam (deletion of the Bam H-1 fragment containing AAV map units 0 to 22 from pAV2) which has a rep$^-$ phenotype. These procedures help to reduce the level of wild type AAV which is generated although it is not yet possible to completely avoid generation of wild type recombinants. However, the yield of packaged vector relative to that of wild type or wild type recombinants can be increased by adjusting the relative amounts of the vector plasmid and the complementing plasmid in the transfections for packaging.

In the example described above, the vector AVHneodlK12 was used to demonstrate that AAV can be used as an efficient, packagable and rescuable vector in eukaryotic cells. However, various other constructions are possible including altering the site of insertion of the selective gene in the AAV vector and the region of AAV which is deleted. For instance, in another construction, pAVXneodlHc23, the neo gene was inserted at the X1 site of pAV2 and the HincII fragment was deleted between the sites Hc2 and Hc3. This is also a packagable and rescuable AAV vector.

The AAV-neo vector rescued from 293 cells by packaging into AAV particles was active in transforming fresh cells to gen$^r$. These results clearly indicated that the AAV vector system is an efficient vehicle, for instance, in screening of cDNA libraries by direct phenotypic selection or for introducing a known gene into cells at high frequency.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A vector comprising part of AAV DNA contained in a plasmid and capable of being packaged into AAV particles and functioning as a vector for stable maintenance or expression of a gene or a DNA sequence in eukaryotic cells when under control of an AAV transcription promotor.

2. The vector of claim 1 wherein said AAV DNA containing plasmid is pAVdlK12.

3. The vector of claim 1 being rescuable from eukaryotic cells either by infection with helper adenovirus or by infection with helper adenovirus and wily type AAV.

4. The plasmid of claim 2 having an American Type Culture Collection accession number 39999.

* * * * *